United States Patent [19]

Kurz

[11] Patent Number: 4,631,028
[45] Date of Patent: Dec. 23, 1986

[54] ORTHODONTIC TOOL

[76] Inventor: Craven H. Kurz, No. 6 North Star, Apt. 106, Marina del Rey, Calif. 90291

[21] Appl. No.: 420,276

[22] Filed: Sep. 20, 1982

[51] Int. Cl.$^4$ ............................................. A61C 7/00
[52] U.S. Cl. .................................................... 433/4
[58] Field of Search ............................ 433/4, 159, 160

[56] References Cited

U.S. PATENT DOCUMENTS 3,755,902 9/1973 Northcutt ............................... 433/4
4,248,587 2/1981 Kurz ....................................... 433/4

FOREIGN PATENT DOCUMENTS 408454 4/1934 United Kingdom ................ 433/160

*Primary Examiner*—Robert Peshock
*Attorney, Agent, or Firm*—Keith D. Beecher

[57] ABSTRACT

A tool in the form of specially constructed pliers for removing orthodontic brackets and tubes which have been adhesively bonded to the lingual surfaces of the anterior and/or posterior teeth for orthodontic treatment. The tool is equipped with a catch having a tip which fits under the edge of the bracket or tube to be removed, and a head which engages the top of the tooth on which the bracket or tube is bonded, and handles are provided respectively connected to the head and tip and which are pivotally coupled to a bracket to turn about respective spaced pivot axes, so that when the handles are squeezed together against a spring-bias the bonded bracket or tube is removed from the lingual surface of the tooth without any tendency to torque the tooth during the process.

2 Claims, 2 Drawing Figures

ORTHODONTIC TOOL

BACKGROUND OF THE INVENTION

Copending application Ser. No. 301,452, filed Sept. 14, 1981, in the name of the present inventor, describes an orthodontic treatment by which brackets and tubes are adhesively bonded to the lingual surfaces of the teeth. Problems arise in effectuating the speedy and easy removal of the adhesively bonded brackets from the lingual surfaces of the teeth after the orthodontic treatment has been completed.

U.S. Pat. No. 4,248,587 which issued Feb. 3, 1981 in the name of the present inventor provides specially constructed pliers which are particularly adapted for removing adhesively bonded brackets and/or tubes from the lingual surfaces of a patient's teeth. The orthodontic tool of the present invention is generally similar to the tool described in the patent.

However, the orthodontic tool of the present invention is somewhat improved as compared with the tool of the patent, in that it is sturdier in its construction and easier to use.

DETAILED DESCRIPTION OF THE ILLUSTRATED EMBODIMENT

Figure 1:
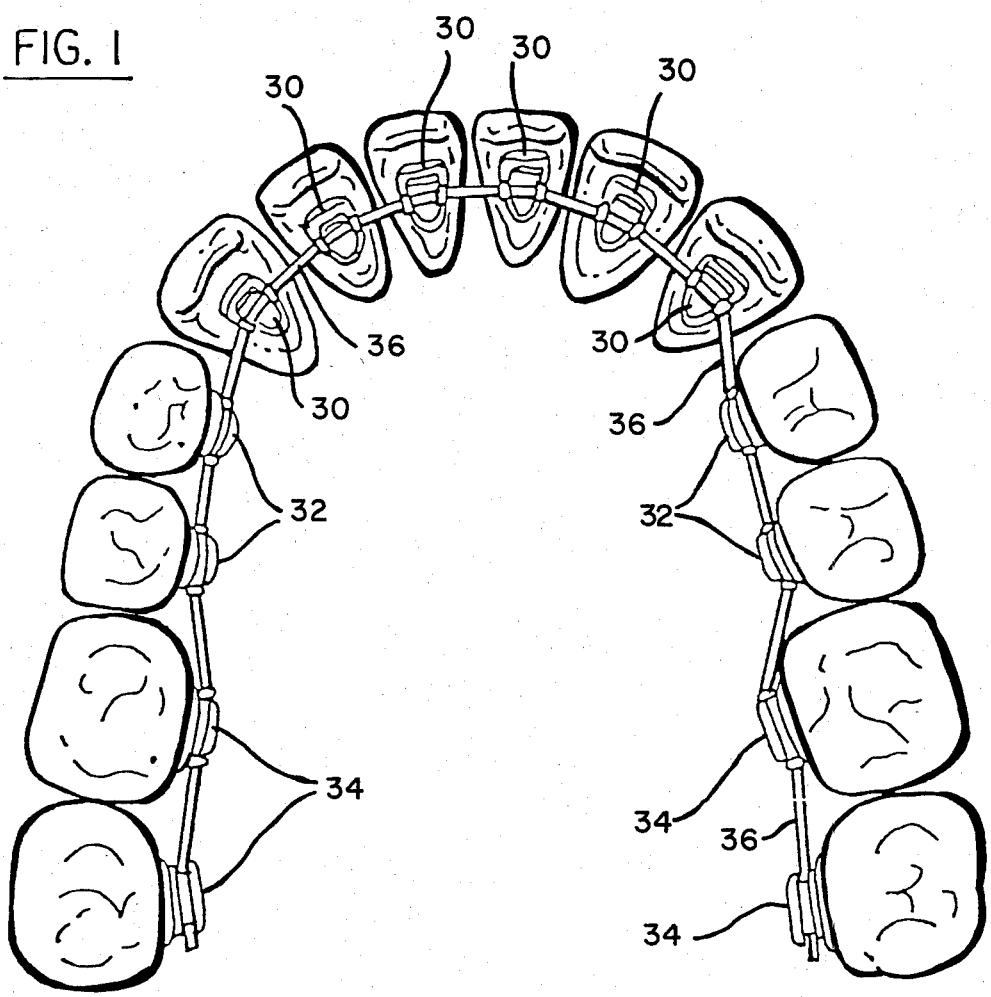
FIG. 1 is a representation of an orthodontic appliance which includes brackets and tubes adhesively bonded to the lingual side of the teeth.

The orthodontic appliance shown in FIG. 1 includes, for example, a number of brackets 30 which are adhesively bonded to the anterior teeth of a patient, and a number of tubes 32 and 34 which are adhesively bonded to the lingual surfaces of the patient's posterior teeth. An arch wire 36 intercouples the brackets and tubes to complete the orthodontic appliance.

The tool of the present invention, as mentioned above, is shown in FIG. 2, and this tool is particularly adapted for removing the adhesively attached brackets 30 and tubes 32 and 34 from the lingual surfaces of the teeth after the orthodontic treatment has been completed.

Figure 2:
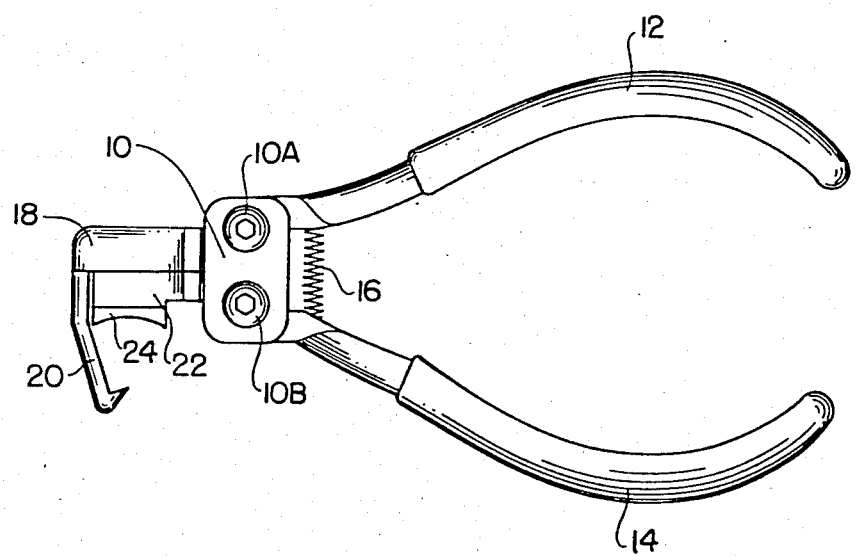
FIG. 2 is a side view of a tool constructed in accordance with the concepts of the present invention, and which is intended to be used in the removal of orthodontic brackets and tubes which have been adhesively bonded to the lingual side of a patient's teeth.

The tool shown in FIG. 2 includes a first section made up of a handle 12 and a first jaw 18, and a second section made up of a handle 14 and a second jaw 22. The first section is pivoted to a bracket 10 by means of a pivot pin 10A, and the second section is pivoted to the bracket 10 by means of a second pivot pin 10B. The pivot pins 10A and 10B are spaced from one another on bracket 10, so that the two sections pivot about respective pivot axes which are spaced from one another.

A spring 16 engages handles 12 and 14 to bias the handles apart, and to bias the jaws 18 and 22 together. A head 24 is mounted on jaw 22, and a depending elongated member 20 is mounted on jaw 18. The head 24 is shaped to engage the top of a tooth when the pliers are inserted into the mouth of a patient, and the elongated member 20 is shaped to extend down over the lingual surface of the tooth and over a bracket or tube bonded to the lingual surface. The member 20 has a tip on its distal end which is shaped to extend under the lower margin of the lingual bracket or tube.

Then, when the handles 12 and 14 are squeezed together against the bias of spring 16, the head 24 bears down on the top of the tooth, and the tip of the elongated member 20 causes the bonded bracket or tube to be stripped upwardly and freed from the tooth. When the pressure is released, the spring 16 biases the handles to their illustrated position, and causes the jaws 18 and 22 to assume their illustrated closed position.

The invention provides, therefore, a simple and sturdy tool, in the form of specially constructed pliers, which are easy to use, and which provide a convenient means for removing adhesively bonded orthodontic brackets and tubes from the lingual surfaces of a patient's teeth after the orthodontic treatment has been completed.

It will be appreciated that while particular embodiments of the invention have been shown and described, modifications may be made, and it is intended in the following claims to cover all modifications which come within the true spirit and scope of the invention.

What is claimed is:

1. A tool for removing an adhesively bonded orthodontic appliance from the lingual surface of a tooth which comprises: a transverse support member; first and second sections pivotally coupled to said support member at transversely spaced pivot points for pivotal movement about spaced pivotal axes, said first and second sections defining first and second handles and upper and lower jaws for the tool; a head portion formed on the lower jaw in position to engage the top of a tooth; and a unitary one-piece elongated depending portion positioned on the upper jaw in overhanging relationship with the lower jaw and having an integral catch member at the distal end thereof in position to extend down behind the tooth and under the edge of the appliance when the head portion engages the top of the tooth for removal of the appliance from the tooth.

2. The tool defined in claim 1, and which includes a spring interposed between said first and second handles for biasing the handles apart and the first and second jaws to a closed position.

* * * * *